(12) United States Patent
Van Criekinge

(10) Patent No.: US 10,119,166 B2
(45) Date of Patent: Nov. 6, 2018

(54) METHODS AND KITS FOR IDENTIFYING AND ADJUSTING FOR BIAS IN SEQUENCING OF POLYNUCLEOTIDE SAMPLES

(71) Applicant: MDxHealth, SA, Herstal (BE)

(72) Inventor: Wim Van Criekinge, Waarloos (BE)

(73) Assignee: MDxHealth, SA, Herstal (BE)

( * ) Notice: Subject to any disclaimer, the term of this patent is extended or adjusted under 35 U.S.C. 154(b) by 197 days.

(21) Appl. No.: 14/767,352

(22) PCT Filed: Feb. 12, 2014

(86) PCT No.: PCT/IB2014/058942
§ 371 (c)(1),
(2) Date: Aug. 12, 2015

(87) PCT Pub. No.: WO2014/125421
PCT Pub. Date: Aug. 21, 2014

(65) Prior Publication Data
US 2016/0017415 A1    Jan. 21, 2016

Related U.S. Application Data

(60) Provisional application No. 61/763,771, filed on Feb. 12, 2013.

(51) Int. Cl.
*C12Q 1/68* (2018.01)
*C12Q 1/6874* (2018.01)
*C12Q 1/6869* (2018.01)
*C07H 21/02* (2006.01)

(52) U.S. Cl.
CPC ......... *C12Q 1/6874* (2013.01); *C12Q 1/6869* (2013.01); *C12Q 2600/154* (2013.01); *C12Q 2600/156* (2013.01)

(58) Field of Classification Search
CPC ............ C12Q 1/6869; C12Q 2545/101; C12Q 1/6874; C12Q 2600/154; C12Q 2600/156
See application file for complete search history.

(56) References Cited

U.S. PATENT DOCUMENTS

2005/0074787 A1* 4/2005 Fan .................. C12Q 1/6827 435/6.11
2006/0275782 A1  12/2006 Gunderson et al.
2010/0035249 A1   2/2010 Hayashizaki et al.

OTHER PUBLICATIONS

Uhlmann, K. et al, Evaluation of a potential epigenetic biomarker by quantitative methyl-single nucleotide polymorphism analysis, Electrophoresis, vol. 23, pp. 4072-4079 (Year: 2002).*

(Continued)

*Primary Examiner* — Teresa E Strzelecka
(74) *Attorney, Agent, or Firm* — Andrus Intellectual Property Law, LLP

(57) ABSTRACT

Disclosed are methods for determining one or more nucleotides at one or more nucleotide positions of a polynucleotide sample, the polynucleotide sample comprising heterogeneous polynucleotides having different nucleotides at the nucleotide positions. The disclosed methods may be utilized to control for sequencing bias during sequencing of the polynucleotide sample. Suitable samples may include patient samples for use in diagnosing, prognosing, and treating the patient.

9 Claims, 10 Drawing Sheets

Specification includes a Sequence Listing.

(56) References Cited

OTHER PUBLICATIONS

Korshunova, Y. et al., Massively parallel bisulphite pyrosequencing reveals the molecular complexity of breast cancer-associated cytosine-methylation patterns obtained from tissue and serum DNA, Genome Res., vol. 18, pp. 19-29 (Year: 2008).*

International Search Report for PCT/IB2014/058942 dated Aug. 27, 2015.

De Grassi et al., "Ultradeep sequencing of a human ultraconserved region reveals somatic and constitutional genomic instability", Jan. 5, 2010, PLoS Biology, Jan. 5, 2010, 8(1):e1000275.

Jiang et al., "Noninvasive fetal trisomy (NIFTY) test: an advanced noninvasive prenatal diagnosis methodology for fetal autosomal and sec chromosomal aneuploidies", BMC Medical Genomics, Dec. 1, 2012, 5(1):57.

Kaminski et al., "MilkProtChip—a microarray of SNPs in candidate genes associated with milk protein biosynthesis—development and validation", Journal of Applied Genetics, Jan. 1, 2005, 46(1):45-58.

International Search Report for PCT/IB2014/058942 dated Jun. 20, 2014.

Written Opinion for PCT/IB2014/058942 dated Jun. 20, 2014.

* cited by examiner

FIG. 5

Analysis of Full Allele Identifies Highly Methylated Members Even for Low Ct Count Sample Designation Number

| # mC | 45409 | 45399 | 45266 | 45402 | 45194 | 45403 | 45406 | 45603 | 45214 | 45257 | 45260 |
|---|---|---|---|---|---|---|---|---|---|---|---|
| 0 | 3507 | 2428 | 1598 | 1876 | 2521 | 4180 | 3882 | 4893 | 2279 | 3778 | 2125 |
| 1 | 1468 | 1666 | 969 | 1163 | 1125 | 2329 | 2344 | 2594 | 1065 | 2037 | 1343 |
| 2 | 512 | 661 | 373 | 499 | 386 | 1038 | 989 | 883 | 372 | 904 | 614 |
| 3 | 210 | 429 | 101 | 221 | 167 | 393 | 365 | 301 | 155 | 473 | 158 |
| 4 | 92 | 184 | 62 | 118 | 81 | 145 | 176 | 140 | 51 | 149 | 73 |
| 5 | 64 | 157 | 44 | 114 | 94 | 100 | 131 | 85 | 43 | 79 | 80 |
| 6 | 49 | 280 | 25 | 55 | 73 | 59 | 242 | 59 | 25 | 47 | 75 |
| 7 | 112 | 381 | 34 | 43 | 46 | 42 | 107 | 42 | 12 | 27 | 34 |
| 8 | 47 | 264 | 15 | 80 | 97 | 53 | 159 | 24 | 18 | 24 | 54 |
| 9 | 22 | 240 | 30 | 56 | 51 | 48 | 68 | 26 | 16 | 15 | 17 |
| 10 | 13 | 157 | 29 | 23 | 16 | 64 | 97 | 19 | 6 | 22 | 12 |
| 11 | 12 | 181 | 39 | 36 | 14 | 57 | 222 | 8 | 4 | 16 | 3 |
| 12 | 7 | 70 | 323 | 30 | 16 | 110 | 125 | 11 | 8 | 11 | 6 |
| 13 | 14 | 142 | 74 | 78 | 69 | 84 | 111 | 11 | 2 | 12 | 6 |
| 14 | 11 | 58 | 20 | 40 | 15 | 29 | 104 | 15 | 4 | 7 | 2 |
| 15 | 9 | 69 | 6 | 19 | 9 | 40 | 18 | 5 | 1 | 7 | 4 |
| 16 | 11 | 146 | 9 | 27 | 1 | 27 | 6 | 9 | 2 | 3 | 1 |
| 17 | 14 | 170 | 13 | 51 | 5 | 170 | 12 | 12 | 1 | 0 | 0 |
| 18 | 34 | 61 | 10 | 7 | 3 | 21 | 41 | 9 | 0 | 1 | 0 |
| 19 | 126 | 179 | 21 | 3 | 1 | 16 | 4 | 64 | 0 | 2 | 0 |
| 20 | 49 | 191 | 24 | 0 | 4 | 96 | 1 | 11 | 0 | 2 | 0 |
| 21 | 116 | 19 | 21 | 0 | 7 | 3 | 1 | 1 | 0 | 0 | 1 |
| 22 | 159 | 46 | 54 | 0 | 8 | 0 | 0 | 0 | 0 | 0 | 0 |
| 23 | 16 | 0 | 250 | 0 | 10 | 0 | 0 | 0 | 0 | 0 | 0 |
| 24 | 22 | 0 | 251 | 1 | 75 | 0 | 0 | 0 | 0 | 0 | 0 |
| Average Ct | 23.45089574 | 8.277326132 | 5.985368088 | 1.334731882 | 1.249178194 | 0.990786456 | 0.810877095 | 0.649990253 | 0 | 0 | 0 |

SEQUENCE LISTING

<160> NUMBER OF SEQ ID NOS: 18

<210> SEQ ID NO 1
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 1
acgtacgtya cgtacgt                                                17

<210> SEQ ID NO 2
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 2
acgtacgtca cgtacgt                                                17

<210> SEQ ID NO 3
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 3
acgtacgtta cgtacgt                                                17

<210> SEQ ID NO 4
<211> LENGTH: 17
<212> TYPE: DNA
<213> ORGANISM: Artificial
<220> FEATURE:
<223> OTHER INFORMATION: Random nucleotide sequence provided for
      illustrative purposes
<220> FEATURE:
<221> NAME/KEY: misc_feature
<222> LOCATION: (9)..(9)
<223> OTHER INFORMATION: n is a, c, g, or t

<400> SEQUENCE: 4
acgtacgtna cgtacgt                                                17

<210> SEQ ID NO 5
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 5
acgtacgtca cgtacgt                                                17

<210> SEQ ID NO 6
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 6
acgtacgtta cgtacgt                                                17

<210> SEQ ID NO 7
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 7
acgtacgtaa cgtacgt                                                17

<210> SEQ ID NO 8
<211> LENGTH: 17
<212> TYPE: DNA
<213> ORGANISM: Artificial
<220> FEATURE:
<223> OTHER INFORMATION: Random nucleotide sequence provided for
      illustrative purposes

<400> SEQUENCE: 8
acgtacgtga cgtacgt                                                17

<210> SEQ ID NO 9
<211> LENGTH: 338
<212> TYPE: DNA
<213> ORGANISM: Homo sapiens

<400> SEQUENCE: 9
cctgctgtct gtttactccc taggccccgc tggggacctg ggaaagaggg aaaggcttcc    60
ccggccagct gcgcggcgac tccggggact ccagggcgcc cctctgcggc cgacgcccgg   120
ggtgcagcgg ccgccggggc tggggccggc gggagtccgc gggacccctcc agaagagcgg  180 ccggcgccgt gactcagcac tggggcggag cggggcggga ccacccttat aaggctcgga   240
ggccgcgagg ccttcgctgg agtttcgccg ccgcagtctt cgccaccagt gagtacgcgc   300
ggcccgcgtc cccggggatg gggctcagag ctcccagc                          338

<210> SEQ ID NO 10
<211> LENGTH: 183
<212> TYPE: DNA
<213> ORGANISM: Homo sapiens

<400> SEQUENCE: 10
gaaaggcttc cccggccagc tgcgcggcga ctccggggac tccagggcgc ccctctgcgg    60
ccgacgcccg ggtgcagcg gccgccgggg ctggggccgg cggagtccg cggaccctc      120 cagaagagcg gccggcgccg tgactcagca ctggggcgga gcgggcggg accacccta    180 taa                                                                183

<210> SEQ ID NO 11
<211> LENGTH: 18
<212> TYPE: DNA
<213> ORGANISM: Artificial
<220> FEATURE:
<223> OTHER INFORMATION: Primer utilized for amplifying human GSTP1 gene

<400> SEQUENCE: 11
cggggtgtag cggtcgtc                                                18

```
<210> SEQ ID NO 12
<211> LENGTH: 21
<212> TYPE: DNA
<213> ORGANISM: Artificial
<220> FEATURE:
<223> OTHER INFORMATION: Primer utilized for amplifying human GSTP1 gene

<400> SEQUENCE: 12
ccgccccaat actaaatcac g                                              21

<210> SEQ ID NO 13
<211> LENGTH: 20
<212> TYPE: DNA
<213> ORGANISM: Artificial
<220> FEATURE:
<223> OTHER INFORMATION: Primer utilized for amplifying human GSTP1 gene

<400> SEQUENCE: 13
gaaagaggga aaggtttttt                                                20

<210> SEQ ID NO 14
<211> LENGTH: 20
<212> TYPE: DNA
<213> ORGANISM: Artificial
<220> FEATURE:
<223> OTHER INFORMATION: Primer utilized for amplifying human GSTP1 gene

<400> SEQUENCE: 14
aaccttataa aaataatccc                                                20

<210> SEQ ID NO 15
<211> LENGTH: 191
<212> TYPE: DNA
<213> ORGANISM: Artificial
<220> FEATURE:
<223> OTHER INFORMATION: Partial sequence of bisulfite-treated and
      amplified human GSTP1 gene

<400> SEQUENCE: 15
gaaagaggga aaggtttttt cggttagttg cgcggcgatt tcggggattt tagggcgttt    60
ttttgcggtc gacgttcggg gtgtagcggt cgtcgggggtt ggggtcggcg ggagttcgcg   120 ggattttta gaagagcggt cggcgtcgtg atttagtatt ggggcggagc ggggcgggat    180
tatttttata a                                                        191

<210> SEQ ID NO 16
<211> LENGTH: 195
<212> TYPE: DNA
<213> ORGANISM: Artificial
<220> FEATURE:
<223> OTHER INFORMATION: Partial sequence of human GSTP1 gene having Y
      degeneracy at CpG positions

<400> SEQUENCE: 16
gaaagaggga aaggtttttt cggttagttg cgcggcgatt tcggggattt tagggcgttt    60
ttttgcggtc gacgttyggg gtgtagyggt ygtygggggtt ggggtyggcg ggagttcgcg   120 ggattttta gaagagcggt yggygtygtg atttagtatt ggggyggagc ggggcgggat    180
tatttttata aggtt                                                    195

<210> SEQ ID NO 17
<211> LENGTH: 197
<212> TYPE: DNA
<213> ORGANISM: Artificial
```

```
<220> FEATURE:
<223> OTHER INFORMATION: Partial sequence of human GSTP1 gene having Y
      degeneracy at CpG positions and including a CC tag

<400> SEQUENCE: 17
gaaagaggga aaggtttttt cggttagttg cgcggcgatt tcggggattt cctagggcgt      60 tttttttgcgg tcgacgttyg gggtgtagyg gtygtygggg ttggggtygg cgggagttcg     120
cgggattttt tagaagagcg gtyggygtyg tgatttagta ttggggygga gcggggcggg     180
attattttta taaggtt                                                    197

<210> SEQ ID NO 18
<211> LENGTH: 15
<212> TYPE: DNA
<213> ORGANISM: Artificial
<220> FEATURE:
<223> OTHER INFORMATION: Primer for amplifying sequence of human GSTP1
      gene having Y degeneracy at CpG positions and including a CC tag

<400> SEQUENCE: 18
ttcggggatt cctta                                                       15
```

METHODS AND KITS FOR IDENTIFYING AND ADJUSTING FOR BIAS IN SEQUENCING OF POLYNUCLEOTIDE SAMPLES

CROSS REFERENCE TO RELATED APPLICATION

The present application is the U.S. national stage of International Application PCT/IB2014/058942, filed Feb. 12, 2014, which international application was published on Aug. 21, 2014, as International Publication No, WO 2014/125421. The International Application claims priority to U.S. Provisional Patent Application No. 61/763,771, filed Feb. 12, 2013, the contents of which are incorporated herein by reference in their entireties.

BACKGROUND

The field of the invention relates to methods for sequencing polynucleotide samples. In particular, the field of the invention relates to methods for identifying for bias in sequencing of polynucleotide samples. The methods may be adapted for identifying and adjusting for bias in sequencing methods utilized for diagnosing, prognosing, and treating patients having a disease or disorder.

Over the last thirty years, detection of genetic mutations and epigenetic modifications has emerged as an important clinical tool in medicine. Mutations and epigenetic changes, such as methylation, have been detected using methods that utilize restriction enzymes (e.g., methylation-specific digital karyotyping (MSDK) and combined bisulfite restriction analysis (COBRA)), the polymerase chain reaction (PCR) (e.g., methylation specific PCR (MSP), heavy methyl PCR, and methylight PCR), hybridization (e.g., epi-microarrays, and bead-arrays), and DNA sequencing (e.g., clonal (pyro/Sanger) sequencing, or synthesis-type sequencing). In particular, advances in DNA sequencing technology that have reduced the cost of DNA sequencing have allowed comprehensive investigation of the genetics and epigenetics of diseases.

However, because of various challenges, genome-wide sequencing using enrichment sequencing has been mainly performed in research settings only and has not been adapted for clinical diagnostics. For example, some of the challenges for genome-wide bisulfite sequencing (BSS) include the fact that clinical samples are highly heterogeneous and contain alleles having varying degrees of methylation. In order to detect methylation at a given position (or the lack of methylation at a given position) with a sufficient degree of sensitivity and specificity requires a relatively large sample size. Therefore, new methods of DNA sequencing that improve the sensitivity and specificity of detection of epigenetic modifications and genetic mutations using relatively small sample sizes are desirable. In particular, these new methods of DNA sequencing should address the challenges of utilizing genome-wide sequencing as a tool in clinical diagnosics.

SUMMARY

Disclosed are methods for determining a nucleotide at a nucleotide position of a polynucleotide sample in which the polynucleotide sample includes heterogeneous polynucleotides having different nucleotides at the nucleotide position. The methods may be utilized for identifying the presence of multiple different nucleotides at the nucleotide position of the heterogeneous polynucleotides.

The methods may include: (a) sequencing a target region of a polynucleotide sample that spans the nucleotide position; and (b) sequencing a set of polynucleotide fragments where the polynucleotide fragments comprise: (i) a polynucleotide sequence corresponding to the target region of the polynucleotide sample; and (ii) a tag for distinguishing the polynucleotide fragments from the target region, which may include a nucleotide tag. The set of polynucleotide fragments typically includes two or more different polynucleotide fragments having the different nucleotides at the nucleotide position of the polynucleotide sample.

In the methods, the target region and the set of polynucleotide fragments may be sequenced in the same or different reaction mixtures. A reaction mixture for sequencing the target region and the set of polynucleotide fragments may include one or more primers that hybridize specifically to the target region and one or more primers that hybridize specifically to the set of polynucleotide fragments. For example, a primer that hybridizes specifically to the set of polynucleotide fragments may include a sequence that hybridizes specifically to a nucleotide tag that is present in the set of polynucleotide fragments.

The methods may include performing deep sequencing. In some embodiments, the methods may include determining the depth of sequencing required to detect a nucleotide at the nucleotide position of the heterogeneous polynucleotides. In other embodiments, the methods may include determining sequencing bias for the different nucleotides at the nucleotide position of the heterogeneous polynucleotides.

The set of polynucleotide fragments utilized in the methods typically includes two or more different polynucleotide fragments having the different nucleotides at the nucleotide position of the polynucleotide sample. In some embodiments, the set of polynucleotide fragments comprises two or more different polynucleotide fragments having a cytosine or a thymine at the nucleotide position of the polynucleotide sample. For example, the set of polynucleotide fragments may comprise or consist of two different polynucleotide fragments having an identical nucleotide sequence except at the nucleotide position to be determined, which is cytosine at the nucleotide position in one nucleotide fragment and is thymidine at the nucleotide position in the other nucleotide fragment. In some embodiments, the set of polynucleotide fragments may comprise equimolar amounts of the two different polynucleotide fragments having a cytosine or a thymine at the nucleotide position of the polynucleotide sample. The methods may include sequencing the set of polynucleotide fragments comprising equimolar amounts of the two different polynucleotide fragments having the cytosine or the thymine at the nucleotide position of the polynucleotide sample, and determining the false-discovery rate for the cytosine or the thymine at the nucleotide position of the polynucleotide sample.

The set of polynucleotide fragments utilized in the methods may include four or more different polynucleotide fragments having an adenine, a guanine, a cytosine, or a thymine, respectively, at the nucleotide position of the polynucleotide sample. For example, the set of polynucleotide fragments may comprise or consist of four different polynucleotide fragments having an identical nucleotide sequence except at the nucleotide position to be determined, which is: adenine at the nucleotide position in one nucleotide fragment; guanine at the nucleotide position in another nucleotide fragment; cytosine at the nucleotide position in another nucleotide fragment; and thymidine at the nucleotide position in another nucleotide fragment. In some embodiments, the set of polynucleotide fragments may comprise equimolar amounts of the four different polynucleotide fragments having the adenine, the guanine, the cytosine, or the thymine, respectively, at the nucleotide position of the polynucleotide sample. The methods may include sequencing the set of polynucleotide fragments comprising equimolar amounts of the four different polynucleotide fragments having the adenine, the guanine, the cytosine, or the thymine, respectively, at the nucleotide position of the polynucleotide sample, and determining the false-discovery rate for the adenine, the guanine, the cytosine, or the thymine at the nucleotide position of the polynucleotide sample.

The disclosed methods may utilize nucleic acid from any source, which may include DNA and RNA. In some embodiments, the polynucleotide sample comprises genomic DNA. In further embodiments, the genomic DNA is treated prior to sequencing with a reagent that selectively modifies non-methylated cytosine residues in the DNA to produce detectable modified residues but which does not modify methylated cytosine residues. In even further embodiments, the nucleotide at the nucleotide position of the polynucleotide sample is a methylated cytosine or a modified residue and the set of polynucleotide fragments comprises two or more different polynucleotide fragments having a cytosine or a thymine at the nucleotide position of the polynucleotide sample. The methods may include calculating a ratio of the number of: (1) the heterogeneous polynucleotides of the polynucleotide sample having the methylated cytosine at the nucleotide position to the number of (2) the heterogeneous polynucleotides of the polynucleotide sample having the non-methylated cytosine at the nucleotide position.

The methods typically include sequencing a target region of a polynucleotide sample that spans the nucleotide position to be determined. In some embodiments, the target region comprises at least about 10 nucleotides of the polynucleotide sample that are 5' to the nucleotide position, and/or the target region comprises at least about 10 nucleotide of the polynucleotide sample that are 3' to the nucleotide position. In other embodiments, the target region comprises at least about 20, 30, 40, 50, or more nucleotides of the polynucleotide sample that are 5' to the nucleotide position, and/or the target region comprises at least about 20, 30, 40, 50, or more nucleotides of the polynucleotide sample that are 3' to the nucleotide position. Accordingly, the target region may include at least about 10, 20, 30, 40, 50, 60, 70, 80, 90, 100, or more nucleotides.

The polynucleotide fragments of the set of polynucleotide fragments typically comprise: (i) a polynucleotide sequence corresponding to the target region of the polynucleotide sample; and (ii) a tag for distinguishing the polynucleotide fragments from the target region, such as a nucleotide tage. In some embodiments, a nucleotide tag comprises a nucleotide sequence of at least about 2, 3, 4, or 5 nucleotides that is not present in the target region of the polynucleotide sample. For example, the nucleotide tag may be utilized to distinguish the target sequence and the polynucleotide fragments, for example, after DNA sequencing is performed or while DNA sequencing is performed (e.g. by utilizing a primer and/or probe that hybridizes specifically to a polynucleotide that comprises the nucleotide tag).

The methods further may be utilized to determine two or more nucleotides at two or more different nucleotide positions of a polynucleotide sample. In some embodiments, the methods may include: (a) sequencing a target region of a polynucleotide sample that spans the two or more nucleotide positions; and (b) sequencing a set of polynucleotide fragments where the polynucleotide fragments comprise: (i) a polynucleotide sequence corresponding to the target region of the polynucleotide sample; and (ii) a tag for distinguishing the polynucleotide fragments from the target region, such as a nucleotide tag. The set of polynucleotide fragments may include different polynucleotide fragments, each having a different possible combination of the two or more nucleotides at the two or more nucleotide positions and representing all different possible combinations of the two or more nucleotides at the two or more nucleotide positions.

In some embodiments where the set of polynucleotide fragments includes two or more different polynucleotide fragments having two or more different nucleotides at two or more different nucleotide positions of the polynucleotide sample, the set of polynucleotide fragments may include different polynucleotide fragments having a cytosine or a thymidine at the two or more nucleotide positions of the polynucleotide sample. In further embodiments, the set of polynucleotide fragments may comprise different polynucleotide fragments, each having a different possible combination of cytosine or thymidine at the two or more nucleotide positions of the polynucleotide sample and representing all different possible combinations of cytosine or thymidine at the two or more nucleotide positions. In this case, the total number of different combinations of polynucleotide fragments (#) in the set of polynucleotide fragments may be represented by the equation $\#=2^N$, where N represents the total number different nucleotide positions and "2" represents the two different possibilities for nucleotides at the different nucleotide positions (i.e., cytosine or thymidine). In even further embodiments, the set of polynucleotide fragments may comprise equimolar amounts of the different polynucleotide fragments, each having a different possible combination of cytosine or thymidine at the two or more nucleotide positions of the polynucleotide sample and representing all different possible combinations of cytosine or thymidine at the two or more nucleotide positions.

In other embodiments, the set of polynucleotide fragments may include different polynucleotide fragments having an adenine, a guanine, a cytosine, or a thymine at the two or more nucleotide positions of the polynucleotide sample. In further embodiments, the set of polynucleotide fragments may comprise different polynucleotide fragments, each having a different possible combination of adenine, guanine, cytosine, or thymidine at the two or more nucleotide positions of the polynucleotide sample and representing all different possible combinations of adenine, guanine, cytosine, or thymidine at the two or more nucleotide positions. In this case, the total number of different combinations of polynucleotide fragments (#) in the set of polynucleotide fragments may be represented by the equation $\#=4^N$, where N represents the total number different nucleotide positions and "4" represents the four different possibilities for nucleotides at the different nucleotide positions (i.e., adenine, guanine, cytosine, or thymidine). In even further embodiments, the set of polynucleotide fragments may comprise equimolar amounts of the different polynucleotide fragments, each having a different possible combination of adenine, guanine, cytosine, or thymidine at the two or more nucleotide positions of the polynucleotide sample and representing all different possible combinations of adenine, guanine, cytosine, or thymidine at the two or more nucleotide positions.

The disclosed methods also may include determining a sequencing bias for a specific allele of an epigenetic locus or genetic locus. The methods may include: (a) sequencing a set of alleles comprising the specific allele to obtain a set of sequences, wherein the set of alleles are degenerate at one or more nucleotide positions; (b) identifying the sequence of the allele in the set of sequences; and (c) calculating the observed frequency of occurrence for the sequence of the allele versus the expected frequency of occurrence for the sequence of the allele. Subsequently, the determined sequencing bias may be utilized to modify the depth of sequencing performed in sequencing methods for detecting the specific allele.

Also disclosed herein are kits for practicing the disclosed methods for determining a nucleotide at a nucleotide position of a polynucleotide sample in which the polynucleotide sample includes heterogeneous polynucleotides having different nucleotides at the nucleotide position. The kits may include oligonucleotide primers: (i) for sequencing a target region of the polynucleotide sample that spans the nucleotide position; and (ii) for sequencing a set of polynucleotide fragments as contemplated herein. The kits further may include the set of polynucleotide fragments. As contemplated herein, the polynucleotide fragments may include a polynucleotide sequence corresponding to the target region of the polynucleotide sample, and the polynucleotide fragments further may include a tag (e.g., a nucleotide tag) for distinguishing the polynucleotide fragments from the target region, for example, after DNA sequencing or during DNA sequencing (e.g., by utilizing a primer and/or probe that hybridizes specifically to a polynucleotide fragment comprising a nucleotide tag). The set of polynucleotide fragments may comprise two or more different polynucleotide fragments having the different nucleotides at the nucleotide position of the polynucleotide sample. The different polynucleotide fragments may be present in the set of polynucleotide frag in equimolar amounts. The kits further may include one or more reagents for performing sequencing of the polynucleotide sample, such as enzymes and buffers.

The disclosed methods and kits may be utilized for diagnosing, prognosing, and treating a patient in need thereof, such as a patient having or suspected of having a disease or disorder. The disclosed methods may include diagnosing and/or prognosing a patient in need thereof and further may include subsequently administering treatment to the patient in need thereof after diagnosing and/or prognosing the patient. The methods contemplated herein may include: (a) requesting an analysis that provides the DNA sequence of a target sequence in a patient DNA sample, where the analysis utilizes the DNA sequencing methods disclosed herein; and (2) subsequently administering a treatment to a patient based on the results of the analysis.

BRIEF DESCRIPTION OF THE DRAWINGS

FIG. 5 illustrates methylation analysis at twenty-four positions via deep sequencing of eleven bisulfite treated samples.

DETAILED DESCRIPTION

Figure 1:
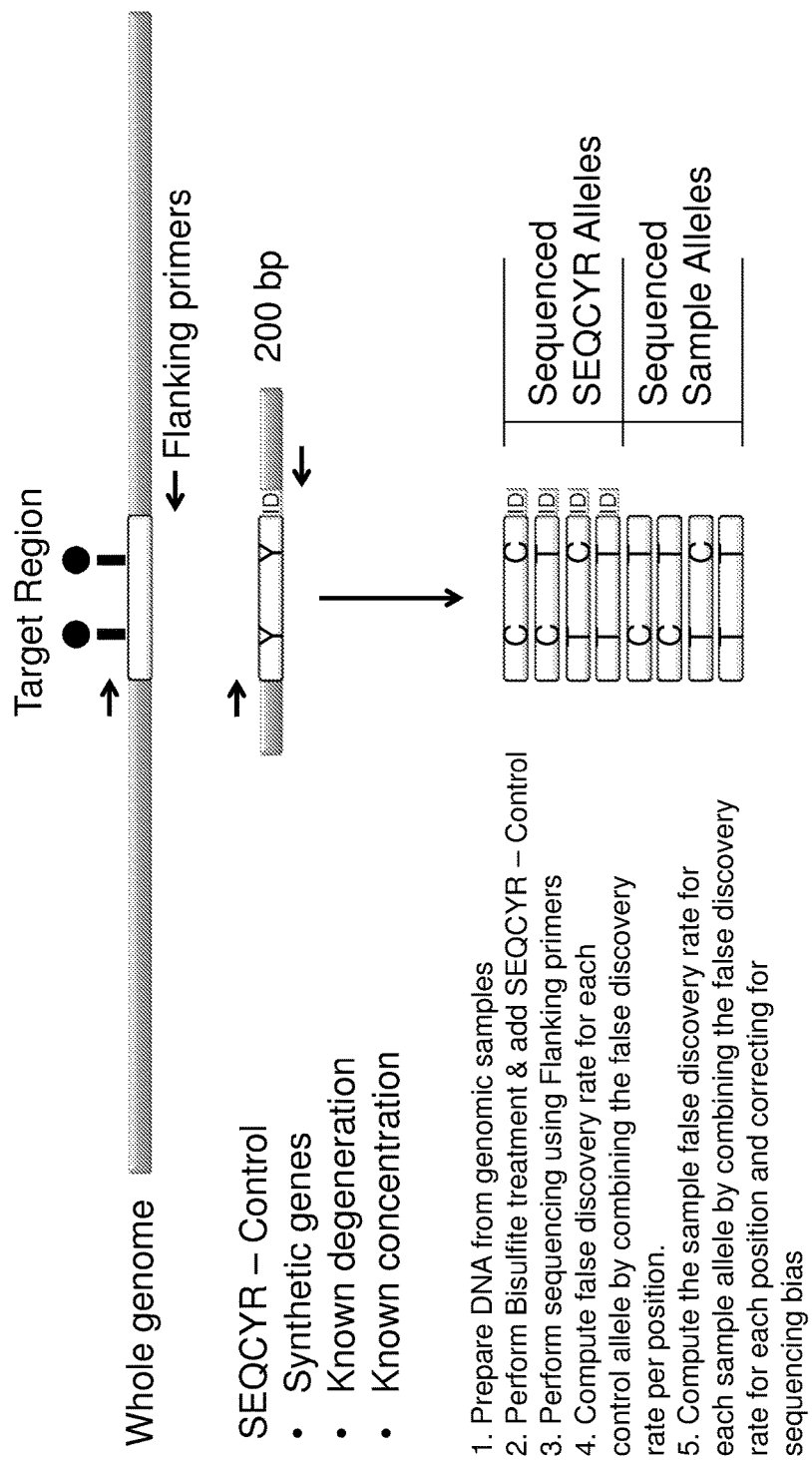
FIG. 1 illustrates one embodiment of the methods contemplated herein.

The present invention is described herein using several definitions, as set forth below and throughout the application.

Unless otherwise specified or indicated by context, the terms "a", "an", and "the" mean "one or more." For example, "polynucleotide" should be interpreted to mean "one or more polynucleotides." The phrase "a nucleotide position" should be interpreted to mean "one or more nucleotide positions."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." For example, "a method that includes a step" should be interpreted to mean "a method that comprises a step." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and permitting the inclusion only of additional components that do not fundamentally alter the nature of the claimed subject matter.

As used herein, the term "patient," which may be used interchangeably with the terms "subject" or "individual," refers to one who receives medical care, attention or treatment and may encompass a human patient. As used herein, the term "patient" is meant to encompass a person at risk for developing a disease or disorder characterized by methylation status of one or more genes associated with the disease or disorder or characterized by genetic mutations associated with the disease or disorder. The "methylation status" of a gene may include the "methylation status" of the promoter of the gene, for example, relative to a control gene. The genetic mutations may be located within the gene associated with the disease or disorder.

As used herein, a patient in need thereof may include a patient having or at risk for developing a disease or disorder including, but not limited to, a cell proliferative disease or disorder (e.g., cancers such as breast cancer, prostate cancer, colon cancer, lung cancer, gall bladder cancer, brain cancer, uterine cancer, ovarian cancer, head and neck cancer, gastric cancer, liver cancer, leukemias, and lymphomas), a neurodegenerative disease or disorder (e.g., Alzheimer's disease, Parkinson's disease, and Huntington's disease), a psychiatric disease or disorder (e.g., schizophrenia and depression), a metabolic disease or disorder (e.g., type 1 or type 2 diabetes), a cardiovascular disease or disorder (e.g., myocardial infarction or stroke), inflammatory diseases or disorders (e.g. arthritis), and immune diseases or disorders.

The disclosed methods may be utilized to diagnose or prognose a patient in need thereof based on methylation status of the promoter region of one or more genes associated with the disease or disorder or characterized by one or more mutations associated with the disease or disorder. As used herein the terms "diagnose" or "diagnosis" or "diagnosing" refer to distinguishing or identifying a disease, syndrome or condition or distinguishing or identifying a patient having or at risk for developing a particular disease, syndrome or condition. As used herein the terms "prognose" or "prognosis" or "prognosing" refer to predicting an outcome of a disease, syndrome, condition, or treatment regimen in a patient.

The disclosed methods may be utilized to treat a patient in need thereof. For example, the disclosed methods may be utilized to diagnose or prognose a patient in need thereof based on methylation status of the promoter region of one or more genes associated with the disease or disorder or characterized by one or more mutations associated with the disease or disorder. Subsequently to the diagnosis or prognosis, the patient may be administered a suitable treatment based on the diagnosis or prognosis of the disease or disorder.

The disclosed methods may be utilized to characterized nucleic acid in a patient sample. The term "sample" or "patient sample" is meant to include biological samples such as tissues (e.g., tissues obtained from biopsies) and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The methods disclosed herein may be applied when performing DNA sequence analysis of a polynucleotide sample. In particular, the methods disclosed herein may be applied when performing DNA sequence analysis of a heterogeneous polynucleotide sample, where the polynucleotide members of the heterogeneous polynucleotide sample have different nucleotides at one or more positions. Suitable heterogeneous polynucleotide samples may include a polynucleotide having a wild-type polynucleotide sequence and a polynucleotide having one or more mutations at one or more positions as compared to the wild-type polynucleotide.

The methods disclosed herein may be applied when performing methylation analysis in particular. For example, the methods disclosed herein may be applied when sequencing a polynucleotide sample after the sample has been treated with an agent that selectively modifies unmethylated cytosine residues and not methylated cytosine residues. Bisulfite treatment commonly is performed to convert unmethylated cytosine residues to uracil residues in a polynucleotide sample. The treated polynucleotide sample then can be utilized as a template for DNA synthesis (e.g., in a PCR amplification or in a sequencing reaction) where uracil residues ultimately are converted to thymidine residues. By performing sequencing of the treated polynucleotide sample, detection of a thymidine residue at a given position versus a cytosine residue will be indicative of an unmethylated cytosine in the original sample or a methylated cytosine in the original sample, respectively.

The methods disclosed herein may be applied to a wide variety of sequencing methods which may include high-throughput or ultra-high-throughput sequencing methods. The methods disclosed herein may include adding an internal control to a polynucleotide sample prior to sequencing a target region in order to determine a nucleotide at a nucleotide position of the polynucleotide sample. The internal control typically includes a set of polynucleotide fragments. Each of the polynucleotide fragments of the set comprises a polynucleotide sequence corresponding to the target region of the polynucleotide sample and a nucleotide tag for distinguishing the polynucleotide fragments from the target region. The set of polynucleotide fragments may include different polynucleotide fragments, each having a different nucleotide at the nucleotide position and representing all different possible combinations of different nucleotides at the nucleotide position. As such, the polynucleotide fragments may be considered to represent a degenerate set. An example of a set of polynucleotides for use as an internal control is illustrated in FIG. 1.

As used herein, "a polynucleotide fragment comprising a polynucleotide sequence corresponding to a target region of the polynucleotide sample" means a polynucleotide fragment that has an identical sequence as the target region of the polynucleotide sample or a polynucleotide fragment that has a sequence that varies only at the one or more nucleotide positions of the target region of the polynucleotide sample which are to be determined via performing the sequencing steps of the methods disclosed herein. For example, where a target region has a sequence ACGTACGTYACGTACGT (SEQ ID NO:1), the polynucleotide fragments of the set may have a sequence such as ACGTACGTCACGTACGT (SEQ ID NO:2) or ACGTACGTTACGTACGT (SEQ ID NO:3). Where a target sequence has C/T degeneracy at N positions, the total number of polynucleotide fragments of the set (#) will be $2^N$, where each degenerate position may be one of two different nucleotides (i.e., C or T). As another example, where a target region has a sequence ACGTACGTNACGTACGT (SEQ ID NO:4), the polynucleotide fragments may have a sequence such as ACGTACGTCACGTACGT (SEQ ID NO:5), ACGTACGTTACGTACGT (SEQ ID NO:6), ACGTACGTAACGTACGT (SEQ ID NO:7), or ACGTACGTGACGTACGT (SEQ ID NO:8). Where a target sequence has A/C/G/T degeneracy at N positions, the total number of polynucleotide fragments of the set (#) will be $4^N$, where each degenerate position may be one of four different nucleotides (i.e., A, C, G or T).

The polynucleotide fragments of the set may possess degeneracy at one or more positions where the polynucleotide sample exhibits variability in sequence at one or more nucleotide positions. In some embodiments, the set of polynucleotide fragments encompasses all possible polynucleotide fragments based on the degeneracy at the one or more nucleotide positions. In further embodiments, the set of polynucleotide fragments comprises an equimolar concentration of each of the different polynucleotide fragments having a different nucleotide at the nucleotide position.

In some embodiments of the present methods, the polynucleotide sample and the set of polynucleotide fragments may be sequenced in the same reaction mixture. In such an embodiment, the polynucleotide sample and the polynucleotide fragments may be present at equimolar concentrations in the reaction mixture.

As used herein, a "SEQ_C_YR" synthetic refers to a synthetic set of templates exhibiting C/T degeneracy at one or more positions. The SEQ_C_YR synthetic gene may be used as an internal control or external control when sequencing a polynucleotide sample exhibiting heterogeneity at the one or more positions based on ultimate conversion of unmethylated cytosines to thymidine.

In a polynucleotide sequence, the designation "Y" is intended herein to mean any pyrimidine (e.g., C or T). The designation "X" as used herein, may be utilized to indicate any nucleotide (e.g., A, C, G, or T).

The polynucleotide fragments of the set disclosed herein typically tags, which may include but are not limited to polynucleotide identification tags. For example, a polynucleotide identification tag may be utilized to distinguish the polynucleotide fragments from the polynucleotides of the polynucleotide sample, for example, after DNA sequencing or during DNA sequencing by utilizing a primer and/or probe that hybridizes specifically to the polynucleotide fragments comprising the polynucleotide identification tag. Suitable polynucleotide identification tags may include nucleotide substitutions, insertions, or deletions relative to the polynucleotides of the polynucleotide sample. Substitutions of 2, 3, 4, 5 or more nucleotides may provide suitable polynucleotide identification tags.

The disclosed methods may be applied to a variety of DNA sequencing methods as known in the art. DNA sequencing processes suitable or adaptable for the disclosed methods may include, but are not limited to, sequencing by synthesis, single-molecule real-time sequencing, ion semiconductor sequencing, pyrosequencing, sequencing by ligation, chain termination sequencing, massively parallel signature sequencing, Polony sequencing, DNA nanoball sequencing, Heliscope single molecule sequencing, Nanopore DNA sequencing, sequencing by hybridization, sequencing with mass spectrometry, microfluidic Sanger sequencing, and microscopy-based sequencing techniques. As such, the disclosed methods may be applied to tradition DNA sequencing methods based on the Sanger sequencing method or the Maxam and Gilbert sequencing method, so-called "first-generation" DNA sequencing techniques, as well as methods that are more amenable to high-throughput analysis, so-called "second generation" and "third generation" DNA sequencing techniques." (See, e.g., Mardis, Ann. Rev. Genomics and Human Genetics, Vol. 9: 387-402 (2008); Metzker, Genome Research, (2005) 15:1767-1776; Moorthie et al., Hugo J. v. 5(1-4), December (2011); and Schadt et al., Human Molecular, Genetics, Vol. 19, No. R2, pp. R227-2490, Sep. 21, 2010; and Shendure et al., Nature Biotechnology 26, 1135-1145 (2008).

EXAMPLES

The following Examples are illustrative and are not intended to limit the scope of the claimed subject matter.

Example 1—Targeted Deep Bisulfite Treatment Sequencing Using an SEQ-C-YR Control Materials and Methods DNA Primers and Samples Methylation of the glutathione-S-transferase gene (GSTP1) was analyzed using the disclosed methods. A sequence on chromosome 11 from genetic position 67351027 to 67351365 corresponding to the GSTP1 gene promoter region was analyzed as follows in underline:

(SEQ ID NO: 9)
CCTGCTGTCTGTTTACTCCCTAGGCCCCGCTGGGGACCTGGGAAAGAGG<u>G</u>

<u>AAAGGCTTCCCCGGCCAGCTGCGCGGCGACTCCGGGGACTCCAGGGCGCC</u>

<u>CCTCTGCGGCCGACGCCCGGGGTGCAGCGGCCGCCGGGGCTGGGGCCGGC</u>

<u>GGGAGTCCGCGGGACCCTCCAGAAGAGCGGCCGGCGCCGTGACTCAGCAC</u>

<u>TGGGGCGGAGCGGGGCGGGACCACCCTTATAA</u>GGCTCGGAGGCCGCGAGG

CCTTCGCTGGAGTTTCGCCGCCGCAGTCTTCGCCACCAGTGAGTACGCGC

GGCCCGCGTCCCCGGGGATGGGGCTCAGAGCTCCCAGC

As such the analyzed region had the sequence:

(SEQ ID NO: 10)
GAAAGGCTTCCCCGGCCAGCTGCGCGGCGACTCCGGGGACTCCAGGGCGC

CCCTCTGCGGCCGACGCCCGGGGTGCAGCGGCCGCCGGGGCTGGGGCCGG

CGGGAGTCCGCGGGACCCTCCAGAAGAGCGGCCGGCGCCGTGACTCAGCA

CTGGGGCGGAGCGGGGCGGGACCACCCTTATAA

Methylation specific primers for these region of the GSTP1 gene were utilized in order to specifically amplify methylated DNA as follows:
GSTP1 MSP Confirm Assay

| PRIMER | SEQUENCE | GENETIC POSITION |
|--------|----------|------------------|
| FORWARD | CGGGGTGTAGCGGTCGTC (SEQ ID NO: 11) | 67351144 |
| REVERSE | CCGCCCCAATACTAAATCACG (SEQ ID NO: 12) | 67351235 |

Flanking primers designed to sequence an ~200 bp region upstream and downstream of the region amplified by the MSP primers were selected as follows:
Targeted Deep BT Sequencing

| PRIMER | SEQUENCE | GENETIC POSITION |
|--------|----------|------------------|
| FL FORWARD | GAAAGAGGGAAAGGTTTTTT (SEQ ID NO: 13) | 67351068 |
| FL REVERSE | AACCTTATAAAAATAATCCC (SEQ ID NO: 14) | 67351263 |

As a SEQ-C-YR template, we designed a set of synthetic, degenerate DNA fragments covering the same region as the TARGETED DEEP BT SEQUENCING region of ~195 bp. However, we added a unique polynucleotide identification (ID) tag to the synthetic, degenerate DNA fragments in order to discriminate between sequence reads obtained by the synthetic, degenerate DNA fragments and the sequence reads obtained by the patient sample.

The bisulfite converted DNA sequence on chromosome 11 from 67351068 to 67351263 is as follows:

(SEQ ID NO: 15)
GAAAGAGGGAAAGGTTTTTCGGTTAGTTGCGCGGCGATTTCGGGGATTT

TAGGGCGTTTTTTTGCGGTCGACGTTCGGGGTGTAGCGGTCGTCGGGGTT

GGGGTCGGCGGGAGTTCGCGGGATTTTTTAGAAGAGCGGTCGGCGTCGTG

ATTTAGTATTGGGGCGGAGCGGGGCGGGATTATTTTTATAA

After incorporation of degeneracy (Y) at positions potentially having a methylated or unmethylated cytosine, the bisulfite converted DNA sequence on chromosome 11 from 67351068 to 67351263 is as follows:

(SEQ ID NO: 16)
GAAAGAGGGAAAGGTTTTTCGGTTAGTTGCGCGGCGATTTCGGGGATTT

TAGGGCGTTTTTTTGCGGTCGACGTTYGGGGTGTAGYGGTYGTYGGGGTT

GGGGTYGGCGGGAGTTCGCGGGATTTTTTAGAAGAGCGGTYGGYGTYGTG

ATTTAGTATTGGGGYGGAGCGGGGCGGGATTATTTTTATAAGGTT

There are nine (9) positions in this target region having C/T degeneracy. As such, the SEQ-C-YR template encompassed a set of synthetic, degenerate DNA fragments having $2^9$=512 members.

As an ID tag for the synthetic, degenerate DNA fragments, a di-cytosine sequence was inserted within the target sequence as follows:

(SEQ ID NO: 17)
GAAAGAGGGAAAGGTTTTTCGGTTAGTTGCGCGGCGATTTCGGGGATTT

CCTAGGGCGTTTTTTTGCGGTCGACGTTYGGGGTGTAGYGGTYGTYGGGG

TTGGGGTYGGCGGGAGTTCGCGGGATTTTTTAGAAGAGCGGTYGGYGTYG

TGATTTAGTATTGGGGYGGAGCGGGCGGGATTATTTTTATAAGGTT

A primer that specifically amplifies DNA comprising the ID tag and which, therefore, can be used to distinguish between the synthetic, degenerate DNA fragments and a patient sample was designed as follows:
Primer to Distinguish Between Amplicons Containing ID Tag

| PRIMER | SEQUENCE | | GENETIC POSITION |
|---|---|---|---|
| FL FORWARD | TTCGGGGATTCCTTA | (SEQ ID NO: 18) | 67351107 |

Samples from cores from biopsies from eleven (11) patients were selected and prepared for methylation analysis from the following list of samples:

| Methylation status | Patient No. | Sample Status |
|---|---|---|
| Highly methylated | 30 | positive control - last negative biopsy |
| | 26 | positive control - last negative biopsy |
| medium low methylated | 27 | positive control - last negative biopsy |
| | 27 | positive control - last negative biopsy |
| | 26 | positive control - positive biopsy |
| | 26 | positive control - last negative biopsy |
| | 26 | positive control - positive biopsy |
| medium high methylated | 29 | positive control - last negative biopsy |
| | 12 | positive control - last negative biopsy |
| | 26 | positive control - positive biopsy |
| | 26 | positive control - last negative biopsy |
| | 64 | negative control |

| Methylation status | Patient No. | Sample Status |
|---|---|---|
| not-methylated (positive at second biopsy) | 22 | positive control - last negative biopsy |
| | 22 | positive control - last negative biopsy |
| | 22 | positive control - last negative biopsy |
| | 22 | positive control - last negative biopsy |
| | 22 | positive control - last negative biopsy |
| not-methylated (positive at second biopsy) | 72 | negative control |
| | 50 | negative control |
| | 67 | negative control |
| | 67 | negative control |
| | 38 | negative control |

Eight (8) of the eleven samples were assigned "positive control" status, and three (3) of the eleven samples were assigned "negative control" status.

Methylation Analysis

As controls, in vitro (IV) methylated DNA was utilized (S7821, Chemicon Inc.), as well as DNA from the human colon cancer cell line HCT 116 DKO. The following kits and reagents also were utilized: EZ DNA Methylation™ Kit, D5001, Zymo Research; FastStart High Fidelity PCR System, 03553400001, Roche; High Pure PCR Cleanup Micro Kit, 04983912001, Roche; Quant-iT™ PicoGreen® dsDNA Assay Kit, P7589, Life Technologies; TruSeq DNA HT Sample Prep Kit A, FC-121-2001, Illumina; TruSeq DNA HT Sample Prep Kit B, FC-121-2002, Illumina; and MiSeq Reagent Kit v2, 15034097, Illumina.

For all samples and IV methylated DNA, 1000 ng was converted via bisulfite treatment using the EZ DNA Methylation™ Kit according to the manufacturer's protocol. Amplicons of the converted DNA then were prepared using the Fast Start High Fidelity PCR System according the manufacturer's protocol and using the following master-mix:

Preparation of Master-Mix

| Item | Amount (ul) |
|---|---|
| PCR Buffer (2x) | 5 |
| Forw primer (10 uM) | 1 |
| Rev primer (10 uM) | 1 |
| Enzyme mix | 0.5 |
| Sample (10 ng/ul) | 1 |
| H2O | 0.5 |

Primers and samples were used as described above.

PCR reactions were performed on the P9700 instrument (Applied Biosystems) per the manufacturer's protocol using the following cycling profile:

PCR ThermaCycler Profile

| | |
|---|---|
| 95° C.; 10 min | 1x |
| 95° C.; 30 sec | 5x |
| 60° C.; 30 sec | |
| 72° C.; 30 sec | |
| 95° C.; 30 sec | 5x |
| 55° C.; 30 sec | |
| 72° C.; 30 sec | |
| 95° C.; 30 sec | 30x |
| 52° C.; 30 sec | |
| 72° C.; 30 sec | |
| 72° C.; 7 min | 1x |
| 4° C.; for ever | |

The length of all amplicons was verified on a Bioanalyzer (Agilent). The prepared amplicons then were quantified using a Quant-iT™ PicoGreen® dsDNA Assay Kit, according to the manufacturer's protocol, and then were purified using High Pure PCR Cleanup Micro Kit according to the manufacturer's protocol. After characterization and purification of all amplicons, both the amplicons derived from a patient sample and the amplicons derived from the synthetic genes, were pooled together in equimolar amounts.

The equimolar mixtures of the amplicons of the patient sample and the amplicons of the synthetic genes then were used to make a sequence ready TruSeq library which was sequenced on Illumina's MiSEQ instrument. All mixtures received a different multiplex identifier (MID) in order to discriminate between all sequenced templates after sequencing. Sequencing was performed using the MiSEQ Reagent Kit v2, according to the manufacturer's protocol.

Results

Figure 2:
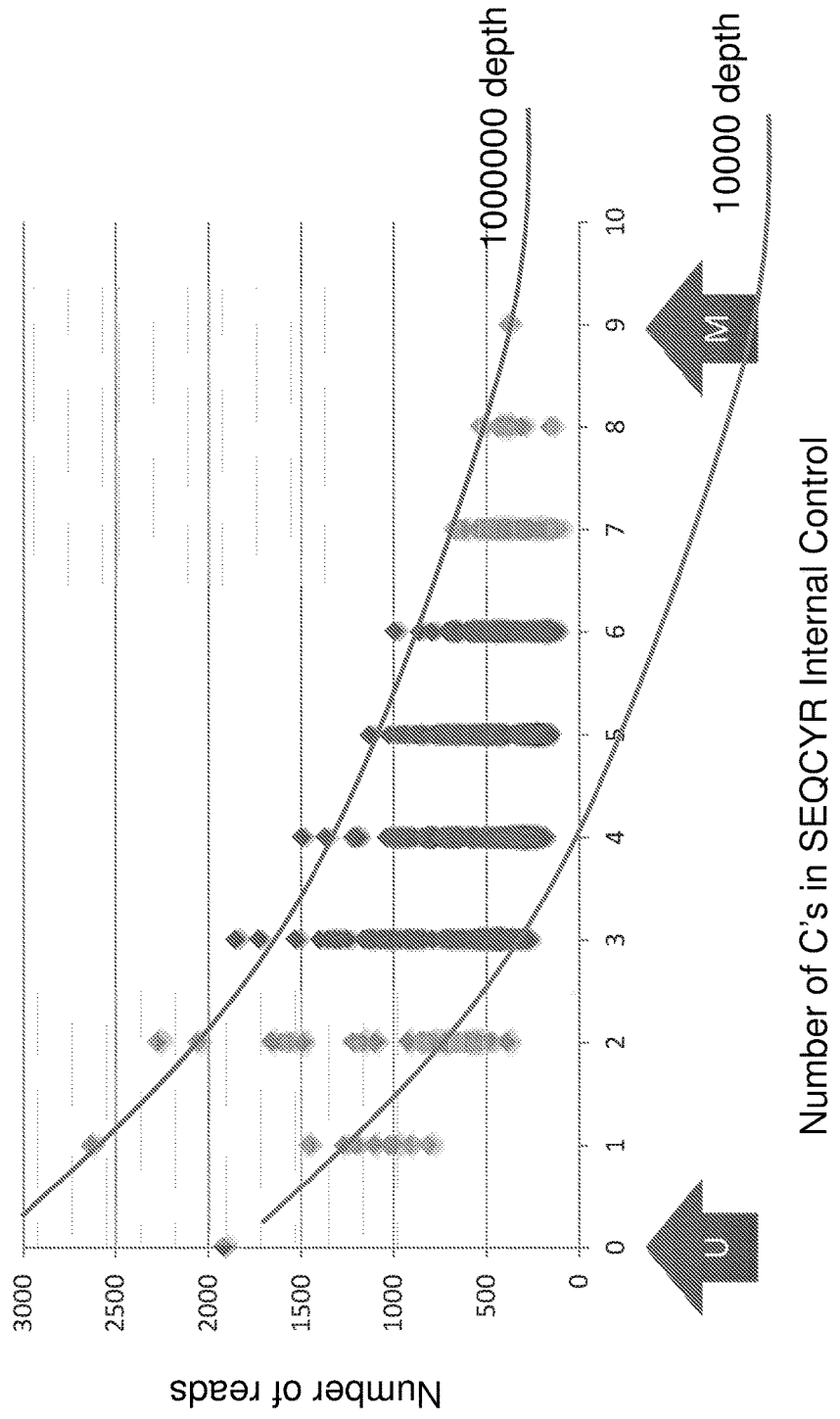
FIG. 2 illustrates sequencing bias for the polynucleotide members of the SEQ-C-YR internal control.

FIG. 1 broadly illustrates the methods performed in the present Example. In FIG. 2, sequencing bias was analyzed by comparing the number of reads for a member of the SEQ-C-YR template versus the number of C's in the template. As shown in FIG. 2, those members of the SEQ-C-YR template having a higher number of thymidines rather than cytosines at a given position exhibited a higher number of reads, indicating that these members were more easily sequenced. The sequencing bias for thymidines over cytosines was determined to be approximately 5. At a sequence depth of approximately $1 \times 10^4$, the template having all thymidines at the given positions gave approximately 2000 reads whereas at a sequence depth of approximately $1 \times 10^6$, the template having all cytosines at the given positions gave approximately 400 reads.

Figure 3:
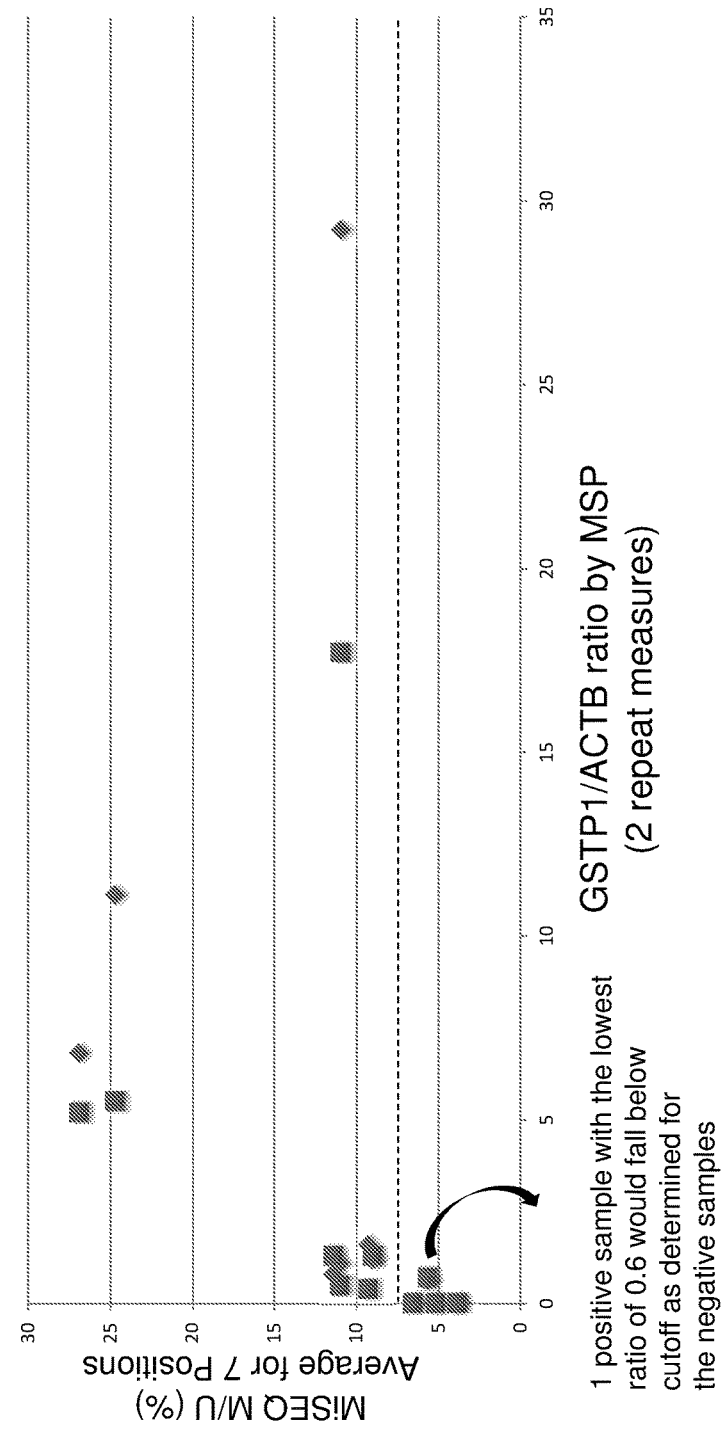
FIG. 3 illustrates the correlation of methylation analysis for the eleven (11) patient samples performed via methylation specific PCR.

FIG. 3 illustrates the correlation of methylation for the eleven (11) patient samples based on performing methylation specific PCR. The methylation percentage was determined at 7 positions using methylation specific primers, and then the percentage methylated/unmethylated (M/U(%)) was plotted versus GSTP1 over actin beta as a control. Seven out of eight of the samples characterized as "positive" fell above the designated cutoff. One of the samples characterized as "positive" as well as the three samples characterized as "negative" fell below the designated cutoff.

Figure 4:
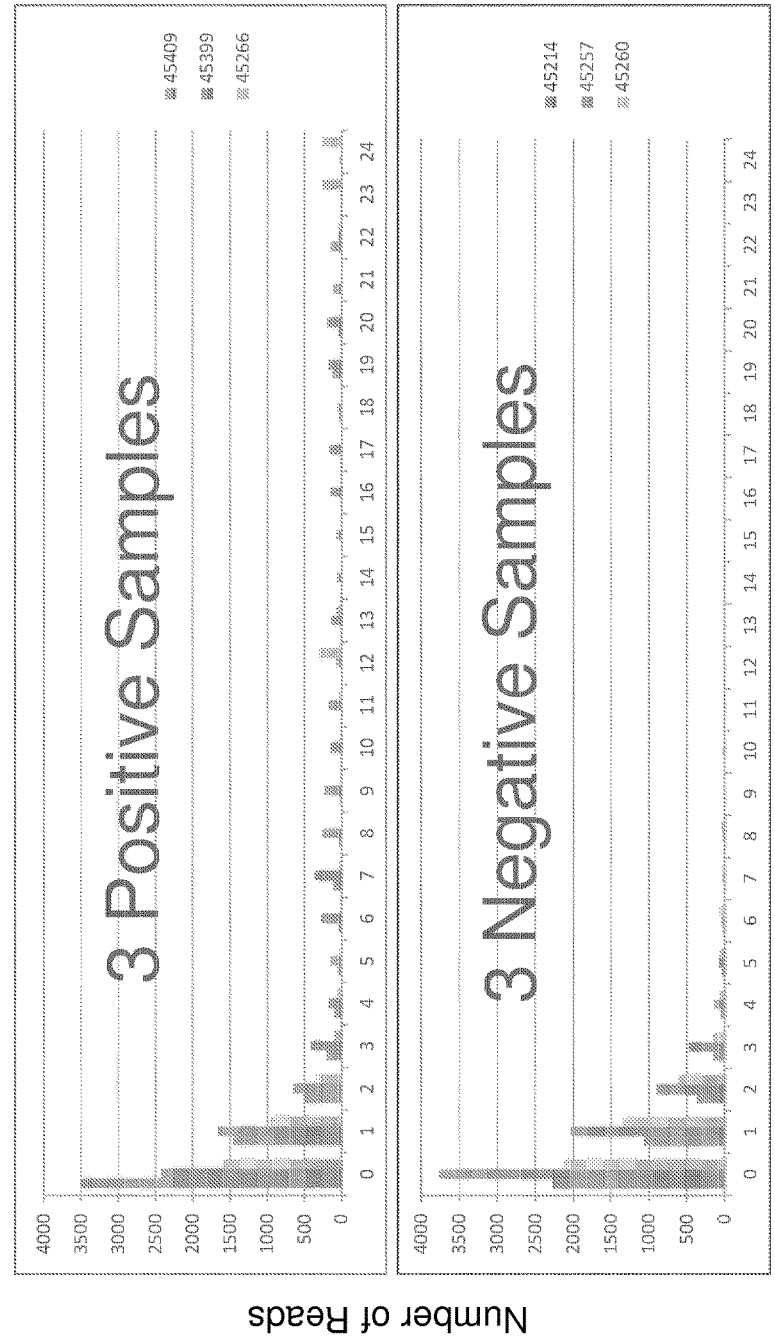
FIG. 4 illustrates methylation analysis at twenty-four positions via deep sequencing of six bisulfite treated samples (three positive, three negative).

Next, three positive samples (Nos. 45409, 45399, and 45266) and three negative samples (Nos. 45214, 45257, and 45260) were fully sequencing through a region covering 24 CpGs. The number of reads for alleles having a given number of C's (i.e., 0-24) was plotted in FIG. 4. As illustrated, the positive samples contained a larger number of alleles illustrating high methylation (i.e., at >~7 positions), whereas, the negative samples contained a low number of alleles illustrating such high methylation.

All eleven samples were subjected to full-allele analysis as illustrated in FIG. 5. Even for the negative samples having a low detectable threshold, it was possible to detect highly methylated alleles within the patient sample.

Figure 6:
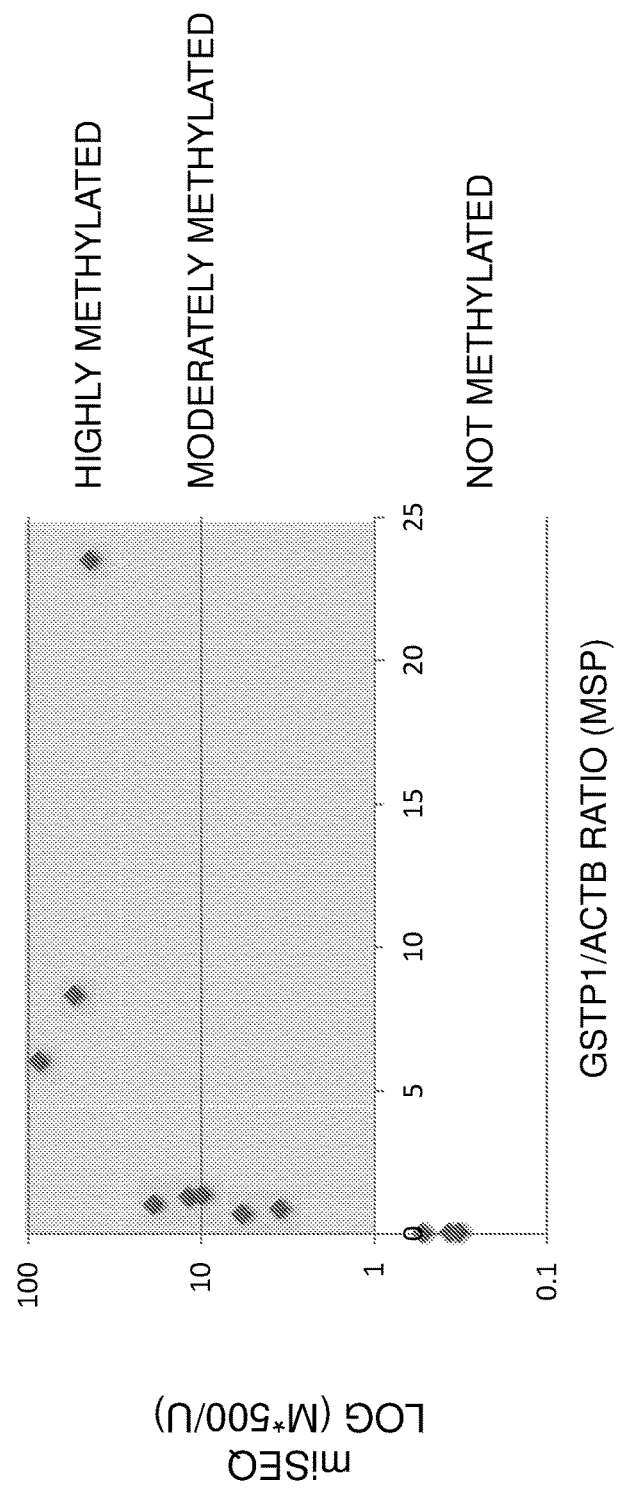
FIG. 6 provides a logarithmic graph of methylation percentage correcting for sequencing bias as illustrated in FIG. 2 versus the ratio of GSTP1 over actin beta as a control.

FIG. 6 provides a logarithmic graph of methylation percentage correcting for sequencing bias as illustrated in FIG. 2 versus the ratio of GSTP1 over actin beta as a control. As illustrated, the three negative samples fell below the cutoff level, and the eight positive samples fell above the cutoff level.

Example 2—SEQ-C-YR: A Correction Method for Next-Generation Sequencing DNA Methylation Data Using a Synthetic Gene Problem Statement and Goal Next-generation sequencing (NGS) could be used as an alternative to methylation-specific PCR (MSP) to determine the DNA-methylation status of one or more genes. Two major advantages are associated with NGS. First, it allows for easier multiplexing and larger panels of genes compared to MSP, since the latter is dependent on the spectral separation of different fluorophores and is often limited to a panel of four genes. Second, the information content obtained with NGS is vastly larger, since it contains information on each individual nucleotide and the frequency of unique alleles. With MSP however, the copies of a methylated gene can be determined using a standard curve, and often a control gene. To this end, methylation-specific primers need to be designed that only detect a methylated allele, but not the unmethylated variant. However, these primers are not entirely specific for the methylated variant and allow wobble at specific location (i.e. local mismatch).

Case Study Overview

The human gene MGMT is applied as a prognostic biomarker in general and predictive biomarker for alkylating agents in glioblastoma multiforme (GBM), and potentially also for lower grade brain tumors. When this gene is methylated, this indicates a better prognosis due to a beneficial response to chemotherapy using an alkylating agent, such as temozolomide, and radiotherapy. Before the advent of NGS, the DNA-methylation status was typically determined with MSP by determining the copies of MGMT and the ACTB control gene and generating a ratio. A higher ratio indicates a higher number of methylated MGMT copies and a higher likelihood that the MGMT gene is silenced through methylation. While this ratio is often multiplied by a factor 1000 for interpretability, a ratio of 2 or higher is considered indicative that MGMT is methylated.

A total of 121 GBM samples from the Linköping University (Sweden) were analyzed using the above-mentioned MSP method and NGS. For NGS, primers were developed that encompassed the entire MSP amplicons, resulting in a final sequence that was 166 bases long. The final analyses of the NGS data can be based on either the methylation frequency or count of one or more C nucleotides or the frequency or number of one or more specific alleles. The NGS amplicons contain a total of 19 CpG dinucleotides (i.e. C's that can be methylated). Relative to the MSP amplicons, this consists of in relative order from 5'→3': four C's that are not part of the MSP amplicons; five C's that are part of the forward MSP primer; seven C's in the internal part of the MSP amplicons; and three C's in the reverse MSP primer. A sequencing depth of ~100000× is envisioned for each sample.

Synthetic Gene Set

A synthetic gene set was created that had degenerate nucleotides at the positions of the C's of interest (i.e. either C or T at the position of interest) and is otherwise referred to as "the SEQ_C_YR synthetic gene." The C's of interest are all part of CpG dinucleotides, which can be methylated, and are part of the MSP amplicon. Therefore, only the four leading C's are not degenerate in the synthetic gene set leaving 15 total degenerate C's. An amplicon mixture having an equimolar concentration of all possible synthetic genes with degenerate nucleotides was prepared and included $2^{15}=32768$ unique alleles. This amplicon mixture was sequenced in the same way as the clinical samples. A technical replicate was run to verify the results.

Figure 7:
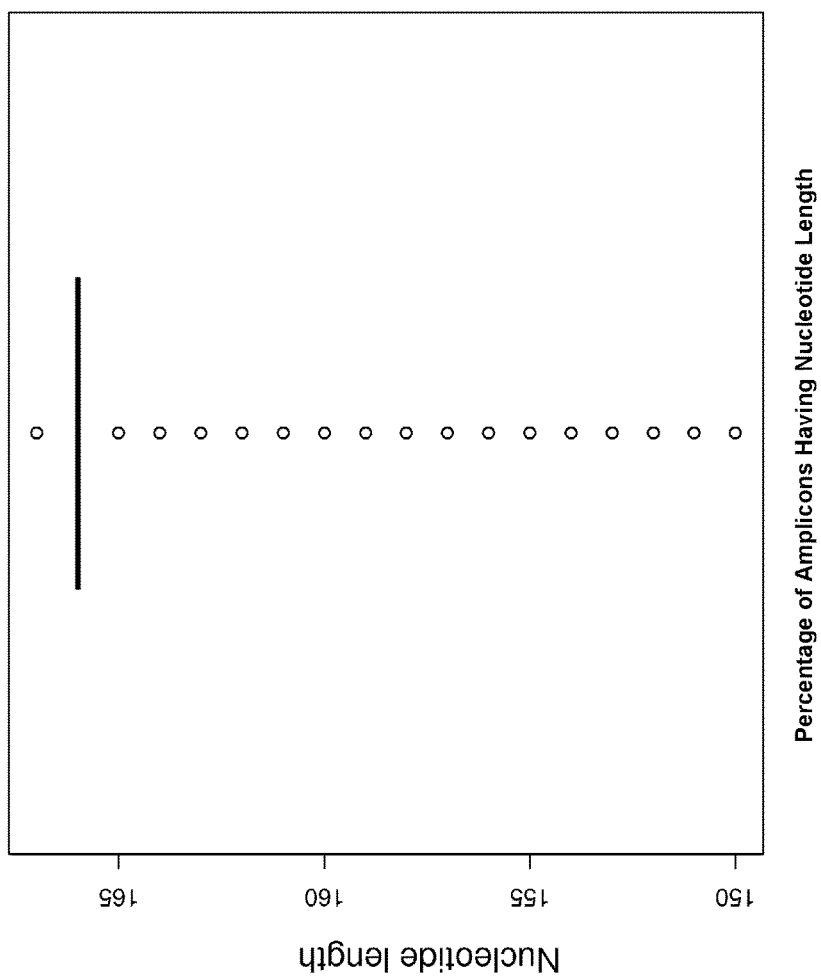
FIG. 7 provides a box-and-whisker plot of the length of amplicons obtained in the experiments of Example 2.

A total sequencing depth of 139665 reads was obtained. As a first quality control, the length of each amplicons was determined. The box-and-whisker plot in FIG. 7 shows that the median, the 25%, and 75% quartile are all of the expected 166 bases in length. Indeed, 95.45% of the sequenced alleles were exactly 166 basepairs (bp) long, while 1.08% was 167 bp long and 3.48% was shorter than 166 bp. This was unexpected, because there is a known link between sequencing quality and the length of a read. It should be noted that all sequences are at least 90% of the length of the complete amplicons.

Figure 8:
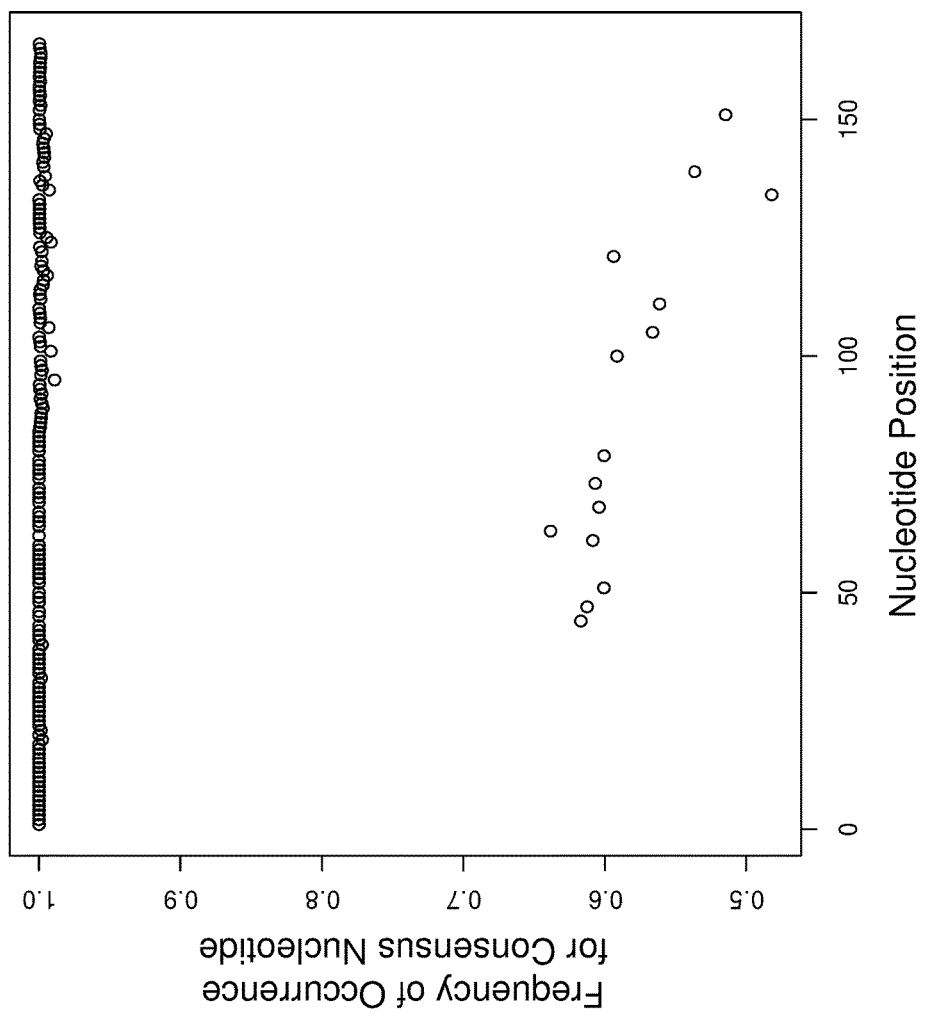
FIG. 8 provides a plot of the frequency of occurrence of the consensus nucleotide (i.e., the most frequently occurring nucleotide) for each nucleotide position of the amplicon.
Figure 9:
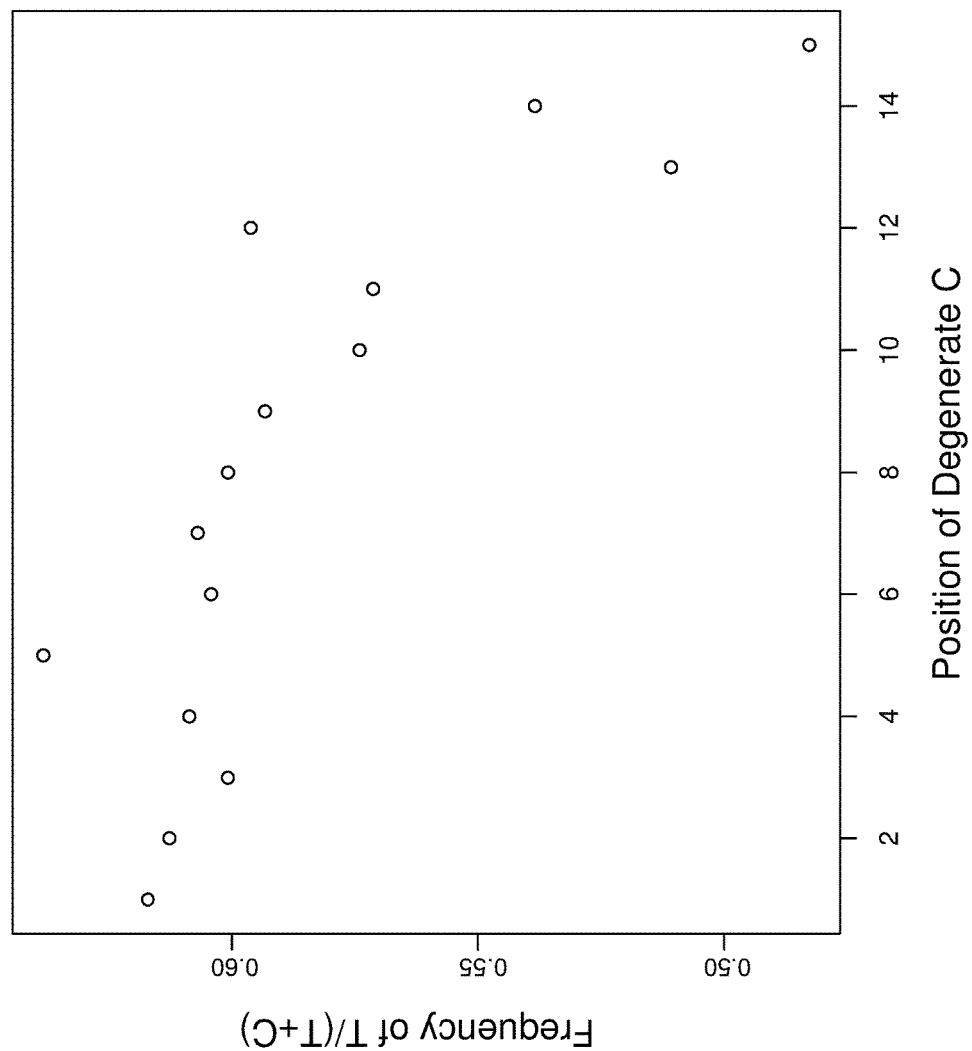
FIG. 9 provides a plot of the count of T at each degenerate position relative to the total count of C's and T's at the degenerate position (i.e., frequency of T's versus C's+T's) for the amplicons of Example 2.

Next, for each position of the amplicons, the observed nucleotide was determined, resulting in 139665 calls for each position. These calls were either one of the nucleotides (A, C, T or G), an undetermined nucleotide (N, no base call), or the absence of a nucleotide in case of a truncated sequence. For each position, the frequency of the consensus nucleotide (i.e. the most prevalent one observed), was determined using all the potential nucleotides as denominator, thereby excluding alleles without a correct base call or truncated alleles. (See FIG. 8). An overall high frequency (i.e. >98%) was observed for all the vast majority of the nucleotides, except for the 15 degenerate C's. For the non-degenerate C's, the consensus frequency was minimally 98.91%. For the degenerate C's, a frequency of ~50% is expected with a mixture of C and T calls (i.e., assuming no bias). However, a sequencing bias was observed (i.e., >0.5) with a higher frequency of unmethylated C's being detected (i.e. T after bisulfite treatment) than methylated C's for most of the degenerate positions. FIG. 9 further illustrates this bias, by depicting the count of a T relative to the count of both C's and T's. While the bias seems to be less for the nucleotides at positions 134, 139 and 151, the mean frequency of T's is 58.37%, significantly larger than the expected 0.5 (p<0.0001; t-test). Similar results were obtained when truncated sequences and non-called nucleotides were taken into account in determining consensus frequency. The minimum consensus frequency determined with this method was 93.87%.

Finally, the non-consensus nucleotides were examined. When only considering called nucleotides, only the 15 degenerate C's reach a high coverage of at least 50000 reads, but never more than 67013. The highest coverage observed for all other nucleotides was 1417 reads or a frequency of 1.01%. When the truncated and uncalled nucleotides were taken into account, the frequency of the non-consensus call was as high as 6.07% for the non-degenerate C's, but all other non-consensus calls had a frequency of less than 3.5%.

Allelic Bias

Next, a detailed allelic resolution was performed which accounted for the full potential of the NGS data. At this stage, because all non-degenerate C's were called with a high consensus, only the degenerate C's were analyzed. Twenty (0.01%) sequences were truncated and did not contain information on the fifteenth and final degenerate C at position 151. The amplicon mixture having an equimolar concentration of all possible synthetic genes contained $2^{15}=32768$ unique alleles. After filtering out all the incomplete alleles (i.e. alleles with undetermined nucleotides at any of the 15 degenerate C positions), a total of 125500 (89.86%) reads were retained (125500/139665). After filtering, 26717 (81.53%) unique alleles could be identified (26717/32768), indicating that almost 20% of the alleles all possible synthetic genes were not detected at this read depth.

Figure 10:
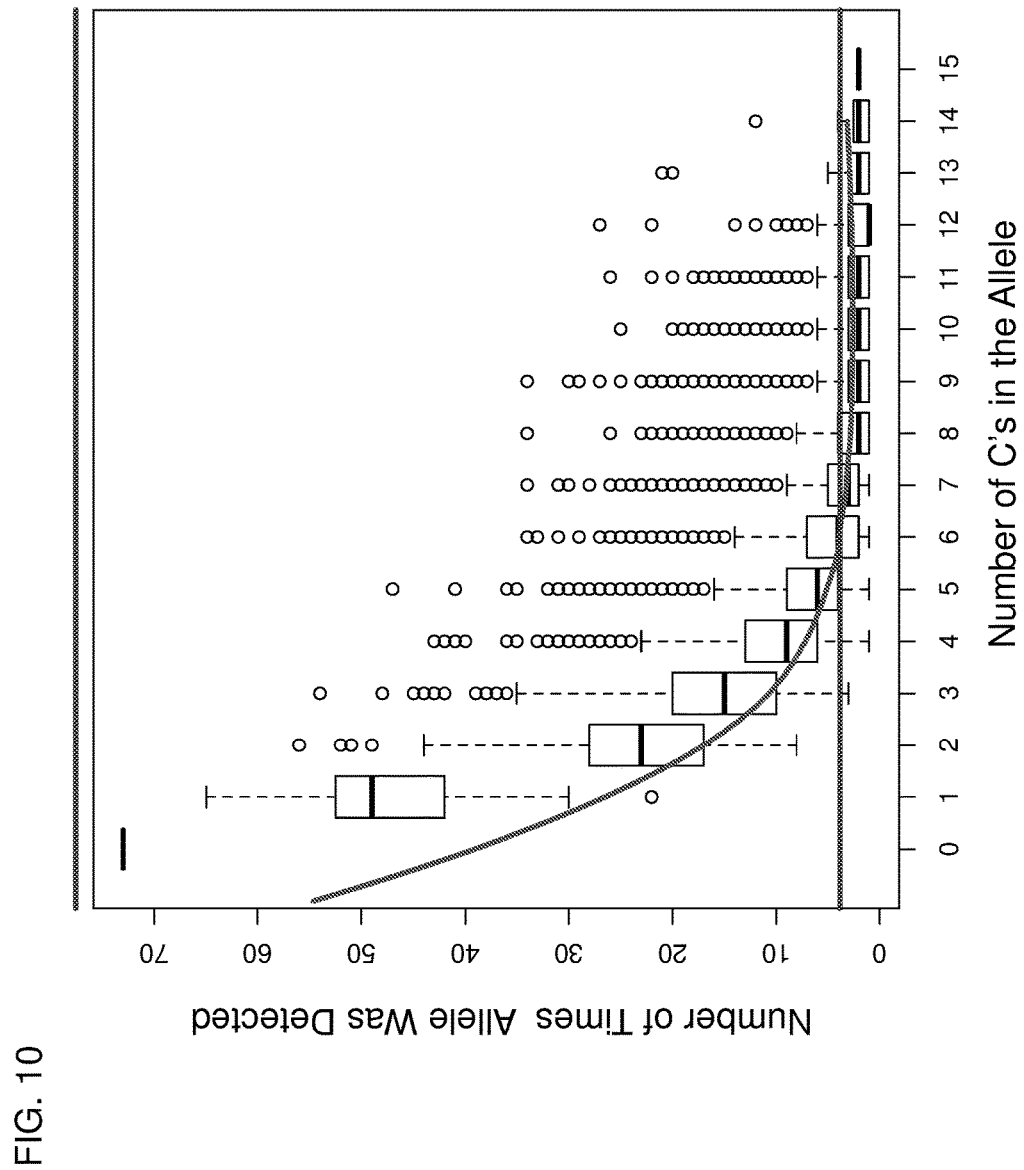
FIG. 10 provides a boxplot of the number of times that an allele was observed versus the number of C's in the allele.

FIG. 10 shows a boxplot with the number of times that an allele was observed (Y-axis) as a function of the number of C's in the allele (X-axis).

At each position there were outliers with higher read depth. However, there is a clear and general inverse correlation between the number of C's present in the sequenced allele and the observed read depth. The loess regression line in FIG. 4 confirms this trend (curved line). The expected read depth is 3.83 per unique allele (flat line), assuming that the distribution would be uniform in the absence of any sequencing bias. The expected read depth increases to 4.26 when all alleles included uncalled bases are included. Hence, there is a clear sequencing bias, both on the individual nucleotide level and even more on the allelic level. Notably, the fully unmethylated allele (i.e. all T's at the degenerate positions) was sequenced 73 times, while the fully methylated allele (i.e., all C's at the degenerate positions) was only observed 2 times. Therefore, the fully methylated allele exhibits a ~35-fold lower depth than the fully unmethylated allele. A loess regression analysis smoothed the large discrepancies but still indicated a sequence bias of 17.5 fold increase for the fully unmethylated allele relative to the fully methylated allele.

Finally, not all unique alleles in the amplicon mixture were detected. In view of the observed sequencing bias observed above, the unsequenced and undetected alleles would preferentially contain more C's than T's. Indeed Table 1 indicates a general trend where alleles containing more C's relative to T's were less likely to be sequenced and detected.

TABLE 1

| # of C's | Expected (E) Number of Alleles Having the Given # of C's | Observed (O) Number of Alleles Having the Given # of C's | O/E |
|---|---|---|---|
| 0 | 1 | 1 | 1.000 |
| 1 | 15 | 15 | 1.000 |
| 2 | 105 | 105 | 1.000 |
| 3 | 455 | 455 | 1.000 |
| 4 | 1365 | 1363 | 0.999 |
| 5 | 3003 | 2967 | 0.988 |
| 6 | 5005 | 4734 | 0.946 |
| 7 | 6435 | 5623 | 0.874 |
| 8 | 6435 | 4980 | 0.774 |
| 9 | 5005 | 3506 | 0.700 |
| 10 | 3003 | 1852 | 0.617 |
| 11 | 1365 | 786 | 0.576 |
| 12 | 455 | 261 | 0.574 |
| 13 | 105 | 57 | 0.543 |
| 14 | 15 | 11 | 0.733 |
| 15 | 1 | 1 | 1.000 |

Conclusion

Using the mixture of synthetic genes, a large sequences bias was observed. Depending on the actual algorithm used to categorize an allele as "methylated" versus "unmethylated," the information obtained by sequencing the mixture can be used to determine the likelihood that a specific allele will be detected based on the depth of sequencing. Therefore, the mixture of synthetic genes may be used as a tool to determine a correct sequencing depth to assure that the methylation status of a patient is categorized correctly.

Application A—Determining Minimum Read Depth Required for Identifying the Fully Methylated Allele As one example, the methylation status of a patient may be categorized as "methylated" only when the completely methylated allele has been observed in sequencing a patient sample (i.e. requiring frequent and dense methylation to categorize the status as "methylated"). By creating and sequencing the mixture of synthetic genes with degenerate C's at all 15 positions, only 2 reads of the fully methylated allele were observed (i.e. all C's at the degenerate position). However, 3-4 reads would have been expected in the absence of any bias. (See FIG. 4). The maximum observed non-consensus nucleotide had a read depth of almost 1500. However, this is a function of the total coverage.

In general, the minimum sequencing depth required for identifying a specific allele may be determined using a binomial test. Based on the analyses done on the non-degenerate nucleotides, a frequency of at least about 2% is required to be assured that the observed sequence does not stem from a sequencing error (i.e. consensus calls). Taking this 2% frequency as a minimum and 1% as the background due to sequencing errors, the binomial test becomes significant as soon as ten alleles are detected in a total of 500 reads (p=0.0377). To reach the minimal reads depth for specific alleles, the overall total coverage, which is already over 100,000, should be increased 2.6- to 5-fold, based on the overall expected frequency and observed frequency of the fully methylated allele.

Application B—Transferring the MSP Assay to the NGS Platform

The MSP assay utilizes two primers: a forward one, which anneals to a site spanning five C's; and a reverse one, which anneals to a site spanning three C's. The seven C's that are in between both primers are part of the final amplicons, but do not affect the end result using MSP (i.e., the amplified sequence between the primers is largely irrelevant to successful amplification in MSP). While the primers are designed to bind to the fully methylated reverse complement at the annealing site, amplification of non-perfect matches may occur, otherwise referred to as "wobble." This so-called "wobble" can occur at any of the C's in the primer positions, except for the C at the 3' end of the primer which needs to match perfectly for amplification to occur. Therefore, "wobble" may occur at 6 of C's in the primer positions.

This results in a total of $2^7*15$ or 1920 alleles that should be taken into account when adapting the MSP result. The $2^7$ is the factor that reflects the non-relevant status of the seven C's between the primers, while "15" is the factor that reflects the number of relevant alleles at the primer sites when "wobble" is taken into account. Based on the total coverage of 139665, it can be calculated that those 1920 alleles should be observed 7353 to 8184 times, depending on whether the total coverage or only the complete sequences (i.e., no uncalled bases, etc.) are taken into account. However, all these alleles taken together are only observed 3072 times, or between 37.5% and 41.8% of the expected frequency. If a coverage of 200 is considered the minimum to call a patient methylated, then the coverage could be lowered to a depth of ~10000 (i.e., 9093) reads per sample. Taking this analysis to individual C nucleotides, the expected frequency of a methylated C in the reverse primer would be $(10/15)*200/9093$ or 1.47%, where "10/15" reflects the number of C's in one of the "wobble" nucleotide positions in the reverse primer out of all amplifiable alleles by MSP (200 expected), assuming that all possibilities are uniformly present. Including background, these are detected in a total of 9093 reads. A binomial test indicates that this is still significantly larger than the ~1% sequencing errors that were observed (p=0.0008). Similar calculations can be made on the allelic level, where ~2 methylated cells in a background of 98 unmethylated cells can be detected.

Application C—Determining Detection Sensitivity

The real sensitivity is significantly larger than 2%, since this is not the limit of detection. When the sequencing errors are considered random and independent of one another and when coverage is sufficiently large, then the errors on the individual nucleotide level can be multiplied, or the detection limit can be calculated as 1%*1%*1%*1%*1%*1%*1%*1% or only 1 in 1e16 alleles. Because the latter coverage cannot be realistically obtained, multiple errors are bound to occur in one and the same allele. To estimate the error, all 8 C positions from the forward and reverse primer may be examined. Sequencing errors may be characterized where an A or G is observed at a position or where position is uncalled. This may result in a slight overestimation of the sensitivity or underestimation of the actual limit of detection, due to the inability to observe C→T or T→C sequencing errors. Only 115 out of the 139665 read in total contain 2 or more such errors (i.e. the observed chance that two sequencing errors occur in the same allele). Using the NGS assay based on the MSP amplicons, a sensitivity of detection of 1 cell in a background of 1214 cells may be obtained (i.e., the detection level below which one cannot be sure that the observed allelic frequency is not due to sequencing errors). This detection sensitivity may be significantly better than the MSP assay, where a fixed ratio is applied to determine whether samples are methylated or not, resulting in a detection limit of 2 cells in a background of 998 unmethylated cells, or almost 2.5 higher than for the NGS assay. However, the fixed ratio for the MSP assay is based on a bimodal distribution of the methylation ratios across a large series of samples.

Summary

A SEQ_C_YR synthetic gene may be utilized as a calibrator in sequencing methods: (1) to determine sequencing bias which often leads to a underrepresentation of the alleles that need to be identified with the assay; (2) to determine minimal coverage that is required to detect specific alleles; (3) to validate the performance characteristics in terms of sensitivity (in the diagnostic sense) and specificity (in the diagnostic and DNA sequence sense); and (4) to assist in construction of an adequate NGS assay with the knowledge that certain alleles may be difficult to detect.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. A method for detecting a cytosine nucleotide or a thymine nucleotide at different nucleotide positions of a polynucleotide sample, the polynucleotide sample comprising heterogeneous polynucleotides having a cytosine nucleotide or a thymidine nucleotide at the different nucleotide positions, the method comprising:
   (a) sequencing in the reaction mixture a target region of the polynucleotide sample that spans the different nucleotide positions;
   (b) sequencing in the same reaction mixture as an internal control a set of polynucleotide fragments comprising a polynucleotide sequence corresponding to the target region of the polynucleotide sample, the polynucleotide fragments further comprising a nucleotide tag for distinguishing the sequenced polynucleotide fragments from the sequenced target region of the polynucleotide sample, the set of polynucleotide fragments comprising all possible polynucleotide fragments having different combinations of a cytosine or a thymidine at the different nucleotide positions, wherein the polynucleotide sample and each of the polynucleotide fragments are present in equimolar amounts in the same reaction mixture; and
   (c) determining that a cytosine nucleotide or a thymine nucleotide is present at the different nucleotide positions of the polynucleotide sample.

2. The method of claim 1, wherein performing sequencing comprises performing deep sequencing.

3. The method of claim 1, further comprising determining depth of sequencing required to detect a cytosine nucleotide or a thymidine nucleotide at the different nucleotide positions.

4. The method of claim 1, further comprising determining sequencing bias for a cytosine nucleotide versus a thymidine nucleotide at the different nucleotide positions of the polynucleotide sample.

5. The method of claim 1, further comprising determining a false-discovery rate for a cytosine nucleotide versus a thymine nucleotide at the different nucleotide positions of the polynucleotide sample.

6. The method of claim 1, wherein the polynucleotide sample is obtained from genomic DNA.

7. The method of claim 6, wherein the polynucleotide sample is prepared by treating the genomic DNA with a reagent that selectively modifies non-methylated cytosine residues in the DNA to produce detectable modified residues but which does not modify methylated cytosine residues.

8. The method of claim 1, further comprising calculating a ratio of the heterogeneous polynucleotides of the polynucleotide sample having a cytosine nucleotide at the different nucleotide positions to the heterogeneous polynucleotides of the polynucleotide sample having a thymidine nucleotide at the different nucleotide positions.

9. The method of claim 1, wherein the nucleotide tag comprises a nucleotide sequence of at least about 2 nucleotides that is not present in the target region of the polynucleotide sample and sequencing the set of polynucleotides fragments comprises utilizing a primer that specifically hybridizes to a polynucleotide comprising the nucleotide tag.

* * * * *